United States Patent [19]
Cassidy et al.

[11] Patent Number: 6,017,340
[45] Date of Patent: *Jan. 25, 2000

[54] PRE-CURVED WIRE GUIDED PAPILLOTOME HAVING A SHAPE MEMORY TIP FOR CONTROLLED BENDING AND ORIENTATION

[75] Inventors: Todd Cassidy, Mocksville, N.C.; John Dimitriou, Stow, Mass.

[73] Assignees: Wiltek Medical Inc., Murray Hill, N.J.; C.R.Bard, Rural Hall, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/790,255

[22] Filed: Jan. 27, 1997

Related U.S. Application Data

[63] Continuation-in-part of application No. 08/349,027, Dec. 2, 1994, abandoned, which is a continuation of application No. 08/317,933, Oct. 3, 1994, abandoned.

[51] Int. Cl.[7] .................................................. A61B 17/36
[52] U.S. Cl. ............................................. 606/47; 606/110
[58] Field of Search ............................. 606/47, 110, 113; 604/281; 206/363; 600/104, 105

[56] References Cited

U.S. PATENT DOCUMENTS

| | | |
|---|---|---|
| 3,633,758 | 1/1972 | Morse . |
| 3,868,956 | 3/1975 | Alfidi et al. ............................. 128/345 |
| 4,325,374 | 4/1982 | Komiya .............................. 128/303.15 |
| 4,474,174 | 10/1984 | Petruzzi ...................................... 128/4 |
| 4,485,812 | 12/1984 | Harada et al. ..................... 128/303.15 |
| 4,545,390 | 10/1985 | Leary ..................................... 128/772 |
| 4,724,836 | 2/1988 | Okada ................................ 128/303.15 |
| 4,846,175 | 7/1989 | Frimberger ........................ 128/303.15 |
| 5,024,617 | 6/1991 | Karpiel ...................................... 606/47 |
| 5,035,696 | 7/1991 | Rydell ...................................... 606/47 |
| 5,075,062 | 12/1991 | Karpiel .................................... 264/173 |
| 5,109,830 | 5/1992 | Cho . |
| 5,163,938 | 11/1992 | Kambara et al. ......................... 606/47 |
| 5,201,732 | 4/1993 | Parins et al. .............................. 606/47 |
| 5,241,970 | 9/1993 | Johlin, Jr. et al. ...................... 128/772 |
| 5,242,462 | 9/1993 | El-Nounon et al. .................... 686/200 |
| 5,275,166 | 1/1994 | Vaitekunas et al. ............... 128/660.03 |
| 5,323,768 | 6/1994 | Saito et al. .................................. 128/7 |
| 5,331,948 | 7/1994 | Utsumi et al. .............................. 128/4 |
| 5,386,818 | 2/1995 | Schneebaum et al. . |

OTHER PUBLICATIONS

C.R. Bard, Wire Guided Papillotomes, p. 21, (undated).
Wilson–Cook, Over–the–Wire Papillotomes, p. 47 (undated).
Abstinct, "Precurved Papillitomes . . . ," Digestive Disease Week, No. 2086, May 14, 1994.
C.R. Bard, Bilisystem, ProForma Papillotomes, Pre–Curved Wire–Guided and Standard.
C.R. Bard, Bilisystem, Sphincterotomy of the Common Bile Duct Using a Pre–Curved Papillotome.

*Primary Examiner*—Michael H. Thaler
*Attorney, Agent, or Firm*—Darby & Darby

[57] ABSTRACT

A papillotome has an elongated sheath and plural longitudinal lumens, a proximal end and a distal end wherein the sheath is sized to be received within an endoscopic lumen. The distal end has a pre-curved shape memory tip for controlling the bending and orientation of the distal end. The pre-curved shape memory tip has a set configuration wherein the tip retains the set curve configuration when the distal end is in a relaxed configuration. A cutting wire having a longitudinal cutting edge is located along the distal end of the sheath which is movable in a cutting plane. The cutting wire is connected to a conductor disposed within one lumen of the sheath. A guidewire is disposed within another lumen of the sheath for guiding the pre-curved shape memory tip within the endoscopic lumen. A third lumen may be provided for delivering or injecting a fluid such as contrast. The package for the papillotome includes curve retention device which retains the pre-curved shape memory tip in the set curve configuration during transit and storage.

17 Claims, 5 Drawing Sheets

PRE-CURVED WIRE GUIDED PAPILLOTOME HAVING A SHAPE MEMORY TIP FOR CONTROLLED BENDING AND ORIENTATION

CROSS-REFERENCE TO RELATED CASES

This application is a continuation-in-part of U.S. patent application Ser. No. 08/349,027, filed Dec. 2, 1994, for PRE-CURVED WIRE GUIDED PAPILLOTOME HAVING A SHAPE MEMORY TIP FOR CONTROLLED BENDING AND ORIENTATION, now abandoned, which is a continuation of U.S. patent application Ser. No. 08/317,933, filed Oct. 3, 1994, for PRE-CURVED WIRE GUIDED PAPILLOTOME, now abandoned.

FIELD OF THE INVENTION

This invention relates generally to sphincterotomes, and more specifically to devices such as papillotomes having a pre-curved shape memory tip which provides controlled bending and orientation during, for example, the cutting of a patient's sphincter (Sphincter of Oddi) and/or papilla (Papilla of Vater).

BACKGROUND OF THE INVENTION

In endoscopic sphincterotomy surgery, sphincterotomes, and more specifically papillotomes, are used in conjunction with an endoscope to provide surgical cutting within a patient. For example, a papillotome may be used to partially cut open the duodenum at the Papilla of Vater for treatment such as removal of common bile duct stones which form an obstruction. Unfortunately, major complications can arise from endoscopic sphincterotomy including bleeding, pancreatitis, perforation, and cholangitis. Bleeding is the most common complication and typically results when the retroduodenal artery is cut. This problem is caused by a lack of control of the surgical equipment used by the physician performing the sphincterotomy.

The typical papillotome, such as disclosed in U.S. Pat. No. 4,485,812 to Harada, et al., includes an electrically conductive wire exposed outside of a tube to act as a cutter. A variety of such sphincterotomes with the wire formed in a bow outside the tube are known as "bowstring" or traction-type sphincterotomes. These devices generally are well known and may contribute to the problem previously described. Shortcomings of this type of papillotome are discussed in U.S. Pat. No. 4,474,174 to Petruzzi, rejecting these more conventional papillotome knives as lacking precise control and providing poor control with danger to adjacent structures during cutting. Instead, the Petruzzi patent suggests an alternative approach in which, rather than having a bowed cutting wire, a pre-bent wire knife having a distal tip is advanced inside a single lumen catheter until it projects from a channel cut through the catheter wall at an angle. The wire knife is connected to a control wire which is manipulated to extend and retract the wire knife into engagement with the tissue. The control wire is fabricated from a helical twisted ribbon-shaped wire. The helical twist provides both a passage way through the lumen for the supply of contrast media, and prevents radial collapse of the catheter walls to prevent the lumen from collapsing.

Several other cutting devices have been proposed with a variety of twisted or braided reinforcing wires in the catheter lumen to reinforce against radial collapse and to maintain the lumen open to allow fluids, such as contrast media, to be supplied to the surgical area. Such devices are illustrated in U.S. Pat. No. 4,325,374 to Komiya, in which a coiled spring is utilized to prevent lumen collapse, and U.S. Pat. No. 4,724,836 to Okada, in which a reinforcing wire is disposed in a fluid lumen to prevent collapse of the lumen when the distal tip is bent. Although these various reinforcing wires may be advantageous for preventing collapse of the lumen, they are not directed to solving the problem set forth above regarding uncontrolled cutting.

Examples of prior art devices commercially available prior to the present invention include the Wilson-Cooke wire guided papillotome, model PTG-30-6-NG and the Bard Interventional Products, models 050049-050052. However, none of these wire guided papillotomes has a pre-curved shape memory tip for controlled bending and orientation and are thus susceptible to the problem of uncontrolled cutting.

SUMMARY OF THE INVENTION

Accordingly, it is an object of the present invention to provide an improved papillotome having a pre-curved shape memory tip which provides controlled bending and orientation.

It is a further object of the present invention to provide a papillotome kit having a pre-curved shape memory tip which provides controlled bending and orientation and a curve retention device for retaining the pre-curved shape memory tip in the set curve configuration.

In carrying out the above and other objects of the invention, in one form, there is provided a papillotome having an elongated sheath with plural longitudinal lumens, the sheath being sized to be received within an endoscopic lumen and into the papilla. The distal end of the sheath has a pre-curved shape memory tip for controlling the bending and orientation of the distal end. The pre-curved shape memory tip has a set configuration wherein the tip retains the set curve configuration when the distal end is in a relaxed configuration. A cutting wire having a longitudinal cutting edge is located along the distal end of the sheath which is movable in a cutting plane. The cutting wire is connected to a conductor disposed within a first lumen of the sheath. A guidewire may be disposed within a second lumen of the sheath for guiding the pre-curved shape memory tip within the endoscopic lumen and into the papilla. A third lumen may be provided for delivering or injecting a fluid such as contrast. The package in which the papillotome is stored includes a curve retention device for retaining the pre-curved shape memory tip in the set curve configuration during transit and storage.

DETAILED DESCRIPTION OF THE INVENTION

Figure 1:
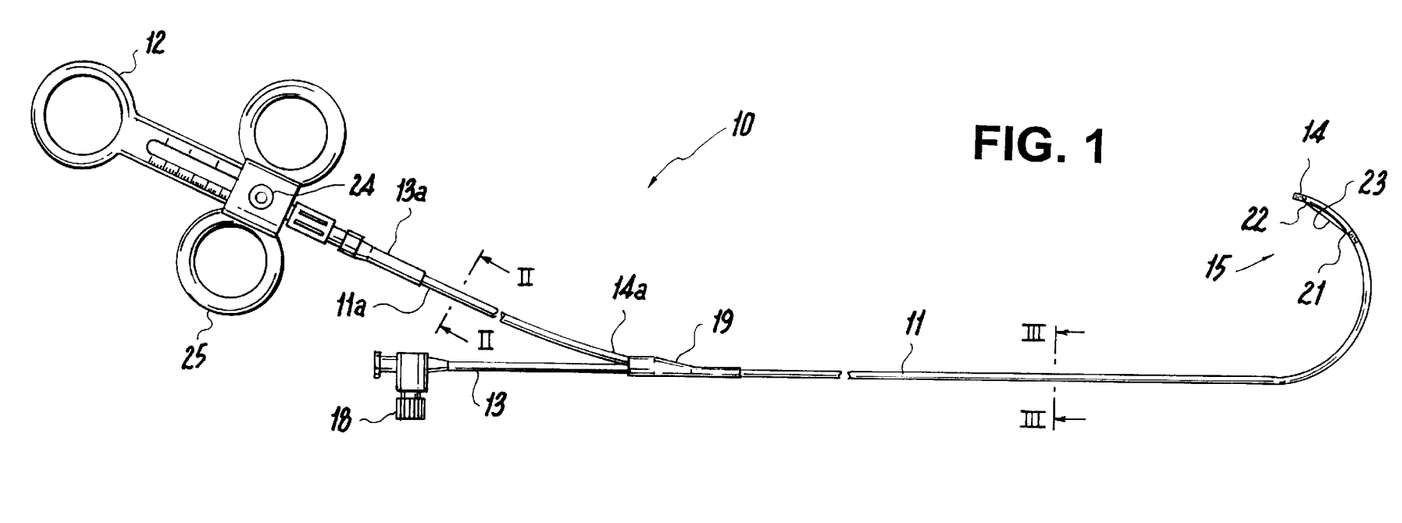
FIG. 1 is a perspective view of a papillotome according to a first embodiment of the invention.
Figure 2A:
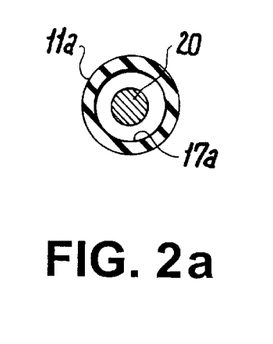
FIGS. 2a and 2b are cross sectional views of the first and second sheaths along lines II—II and III—III, respectively.
Figure 2B:
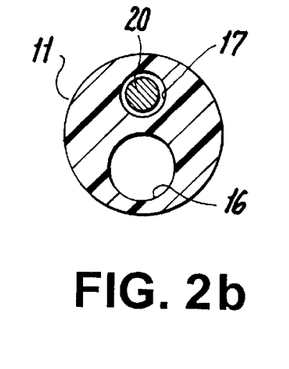

Referring to FIGS. 1 and 2, a preferred sphincterotome, or more specifically, a papillotome 10 is shown having a pre-curved shape memory tip 15 in accordance with a first embodiment of the present invention. The papillotome 10 comprises interconnected first and second sheaths 11 and 11a having proximal and distal ends 13, 13a and 14, 14a, and a manipulator control handle 12 connected to the proximal end 13a of the second sheath 11a. Manipulation of the control handle 12 enables the distal end 14 of the first sheath 11, having a pre-curved shape memory tip 15, to be maneuvered during surgery with controlled bending and orientation.

The first sheath 11 comprises first and second through lumens 16 and 17 which are open at the distal end 14 and coupled to a fitting 18 at the proximal end 13. The fitting 18 may be coupled to a source of fluid, such as fluoroscopic contrast media, to supply the contrast media into the patient through the first lumen 16. The second sheath 11a comprises a single through lumen 17a, which is coupled to the lumen 17 of first sheath 11 to form a continuous channel consisting of both lumens 17 and 17a. The sheaths 11 and 11a may be retained by a sleeve 19 made of shrink tubing.

A wire 20 is disposed within the channel of both lumens 17 and 17a and exposed between first and second locations 21 and 22 to create an electrically conductive cutting wire 23 at the distal end 14 of the first sheath 11. For example, wire 23 may be a braided or monofilament wire. At the proximal end 13a of the second sheath 11a, the electrically conductive wire 20 is connected to a terminal 24, so that a high frequency, monopolar electrical current can be supplied to the cutting wire 23 as is well known in the art. The manipulator control handle 12 includes a movable handle portion 25 which may be drawn proximally to apply tension on the conductor wire 20 and cause the cutting portion 23 to pull tight as is known in the art. Manipulation of the handle portion 25 also controls bending of the pre-curved tip 15 when the wire 20 is pulled.

The sheaths 11 and 11a preferably comprise Polytetrafluoroethylene (PTFE) with the lumen 16 having a diameter of 0.040"±0.003" to allow passage of a 0.035" guidewire (typical in the industry). The lumen 17a, which contains the cutting wire 23, preferably has a diameter of 0.026"±0.003", the diameter of sheath 11a being 0.096"±0.003". The lumen 17 preferably has an inner diameter of 0.026"±0.003". The cutting wire 23 preferably comprises 302 stainless steel having a 0.012" diameter±0.004" while the wire 20 preferably comprises 304 stainless steel having a 0.020" diameter±0.002".

Figure 3A:
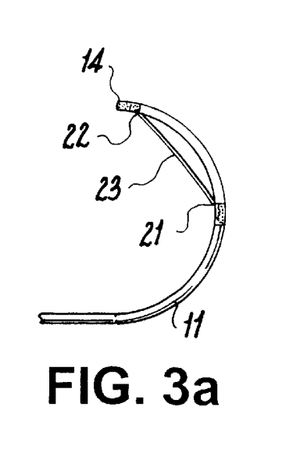
FIGS. 3a–3c are side views of the cutting wire of the papillotome of FIG. 1 at various locations along the distal end according to the invention.
Figure 3B:
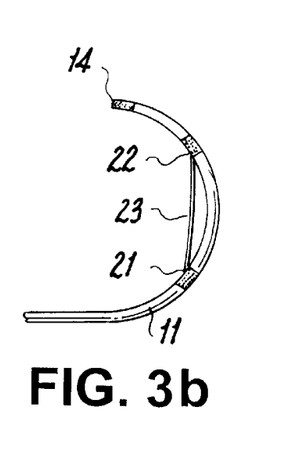
Figure 3C:
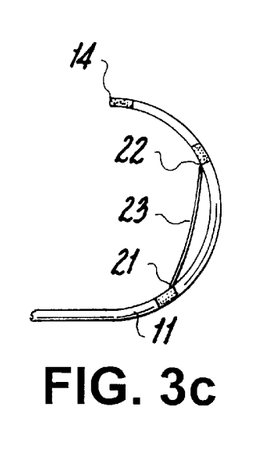

Referring to FIGS. 3a–3c, the cutting wire 23 may be positioned at different locations along the pre-curved tip 15 and may also be of various lengths by changing the locations of proximal and distal openings 21 and 22. The length of the tip may also be changed to provide for different length tips and different length cutting wires as is conventional. In FIG. 3a, the cutting wire 23 is positioned at the distal end 14 of the inner radius of the pre-curved tip 15. In FIGS. 3b and 3c, the cutting wire 23 is positioned along the center of the inner radius of the pre-curved tip 15; however, the cutting wire 23 of FIG. 3c is longer than the cutting wire 23 of FIG. 3b and thus able to remove a larger amount of tissue.

Figure 4:
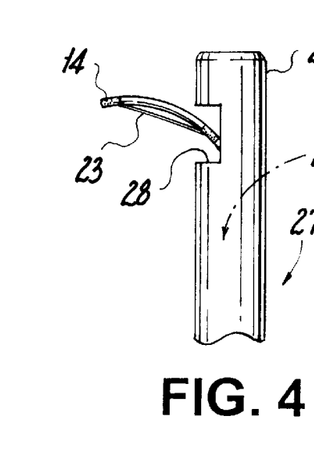
FIG. 4 is an enlarged side view of the cutting wire in the preferred 12 o'clock orientation of the papillotome of FIG. 1 shown exiting the endoscope.

FIG. 4 illustrates how the invention is used. The distal end 14 of the papillotome 10 is advanced within a lumen 26 of an endoscope 27 until it protrudes from an opening 28 at the distal end 29 of the endoscope. During a papillotomy, the distal end 29 of the endoscope 27 is bent at approximately 90 degrees. When the distal end 14 of the papillotome 10 is placed within the lumen 26 of the endoscope 27, the pre-curved tip 15 flexes into a semi-straightened shape. Upon reaching the angled portion of the lumen 26, the pre-curved tip 15 relaxes back to its pre-curved shape. As the papillotome 10 is pushed further into the angled portion of the endoscope 27, the pre-curved tip 15 continues to relax back into its pre-curved shape which causes the tip 15 to steer itself. The progression of the tip 15 into the angled portion of the endoscope 27 and the subsequent relaxing of the tip's pre-curved shape causes the tip 15 to orient automatically into the condition shown in FIG. 4 which is known as the "12 o'clock" position, and which is the optimal position for performing a papillotomy as is well known in the art. Thus, the pre-curved shape memory of the tip 15 tends to resist movement of the cutting edge out of the desired cutting plane which enables the papillotome 10 to approach the papilla in the desired angle for ease of cannulation and a consistent 12 o'clock papillotomy.

Figure 5:
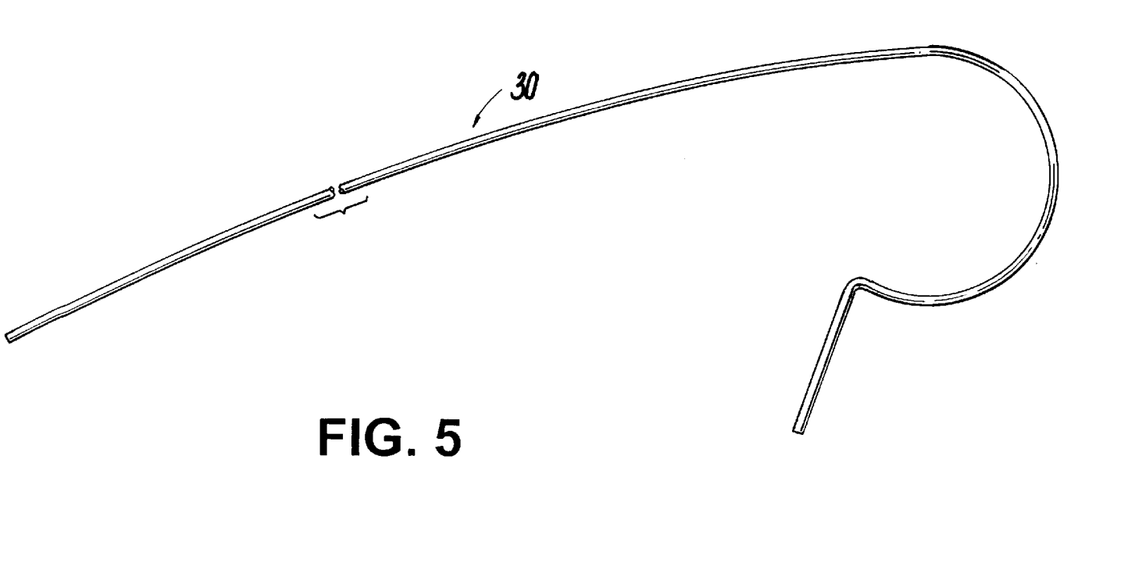
FIG. 5 is a side view of the continuously curved mandrel according to the invention.

In the preferred embodiment, the curved shape-memory tip is formed using a continuously curved mandrel 30 to allow for consistent processing with reproducible curvature, so that the cutting wire 23 can be positioned accurately on the inner radius of the curvature to avoid torsional effects and misalignment. In a specific embodiment, a straight mandrel was formed of 304 stainless steel with a diameter of 0.038". To form the pre-curved shaped memory tip 15, the mandrel is inserted into the lumen 16 and a second mandrel (not shown) with an outer diameter of 0.020" inserted into the smaller lumen 17. The sheath 11 is then inserted into a pre-heated tapering mold with a mold temperature of 400° F.±5° F. After heating, approximately 4.5" of the tapered tubing is cut and a 0.035" mandrel inserted into the tip 15 for support. The tip 15 is then buffed until all edges are rounded and smooth. First and second plugs with diameters of 0.038" and 0.020" are inserted into first and second lumens 16 and 17, respectively.

The wire 20 and cutting wire 23 are prepared by welding a 0.020" wire 20 to a two-foot piece of 0.012" braided wire 23. The weld joint is buffed until the joint is the same diameter as the 0.020" wire and a 25 gauge hole punch is used to make the cutting wire holes 21 and 22 on the shaft 11. A 0.010" mandrel is inserted into the small lumen 17 prior to the hole punching.

The tubing is preferably cut to approximately 210 cm with each cut made at a sharp angle of approximately 25° so that the angle leads toward the large lumen 16. A five mm notch is cut into the tubing 7 cm from the end of the tubing and also into the small lumen 17. A 0.020" wire is placed into the small lumen 17 prior to making the cut to prevent overcutting. Approximately 1 cm of the end of the tubing is buffed and etched and the small lumen 17 is plugged by injecting a UV glue approximately 1 cm and cured for ten seconds.

The wire 20 is then inserted into the proximal end 13 of the lumen 17. The wire 20 is passed through the lumen 17 until the wire 20 reaches the notch on the sheath 11. The tubing is bent and the wire advanced until the wire exits the notch. A small bend is placed in the end of the wire which is then pulled back into the notch.

An 11 gauge collet is placed over the tubing and the notches are aligned with openings in the collet. Using the collet, the wire 20 is pulled back out through the notch. A 23 gauge collet is then loaded over the cutting wire 23. The wire is held while the collet is advanced into the lumen 17 of the tubing as the wire is pulled into the tubing. The wire is pulled until a one-foot section of the braided wire is within the sheath 11.

A 5.5 cm piece of 3/16" shrink tubing is placed onto the sheath above the 11 gauge collet. A double luer, which has been drilled out with a #38 bit, is placed onto the 0.038" mandrel gage. The mandrel gauge is placed into the large lumen 16 and an epoxy applied to the etched area. The luer lock is positioned onto the glued area and the tubing positioned so that it adjoins the gauge with the side port exposed. A shrink tubing is then placed over the luer fitting. An 18 cm piece of 9 FR Teflon is cut and placed onto a 15 gauge luer lock. A sleeving is placed onto the sheath and positioned over an 11 gauge collet. The luer fitting covered with shrink tubing is slid over the wire and positioned over the notch so that it covers this joint. The sleeving is then heat shrunk into place and cooled afterwhich any excess glue is removed from the sheath and the wire.

The handle 12 is assembled to the sheath 11a using a luer adapter as is well known in the art. The wire is inserted into the tip of the handle 12 and through side holes in the pin until it reaches the back portion of the handle slide. A 90° bend is placed in the end of the wire and the wire pulled back until the bend is against the pin. A spring pin (not shown) on opposite side of the terminal 24 is inserted using a standard press which exerts a force of approximately 145 inch-pounds.

A luer lock is inserted into the luer lock adapter using an epoxy as is well known in the art. The finger rings 25 are positioned toward the sheath 11 while the braided wire 23 is positioned next to the distal end 14. At the distal opening 22, a 135° bend is made in the braided wire and inserted into the distal opening 22. Using a syringe and a 25 gauge needle with UV glue, the needle is placed into the small lumen 17 and the glue injected under the cutting wire and cured for approximately 30 seconds.

The papillotome 10 is then placed over the continuously curved mandrel 30 (FIG. 5) with the cutting wire 23 on the inside of the pre-curved tip 15. A piece of the teflon sheath is placed over the tip 15 and the area of the sheath 11 to be curved. The sheath 11 is placed into a fluidized bath for five seconds having a temperature between 380° F.–420° F. The sheath 11 is cooled immediately afterward by dipping the sheath 11 into water at room temperature. The cover sheath is then removed and discarded and the mandrel 30 is removed.

Figure 6A:
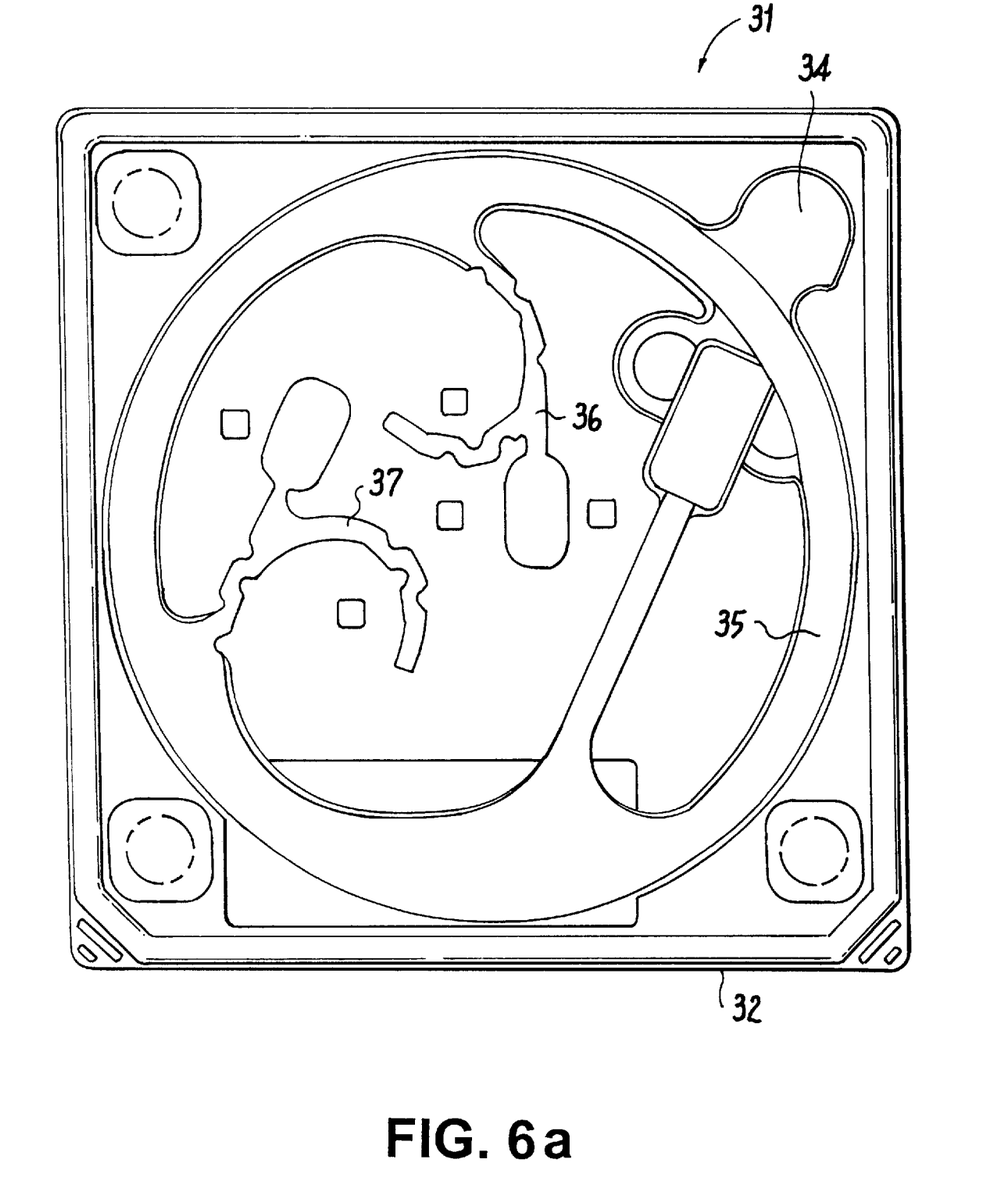
FIGS. 6a and 6b are top plan views of the bottom and top trays of a preferred package according to the invention.
Figure 6B:
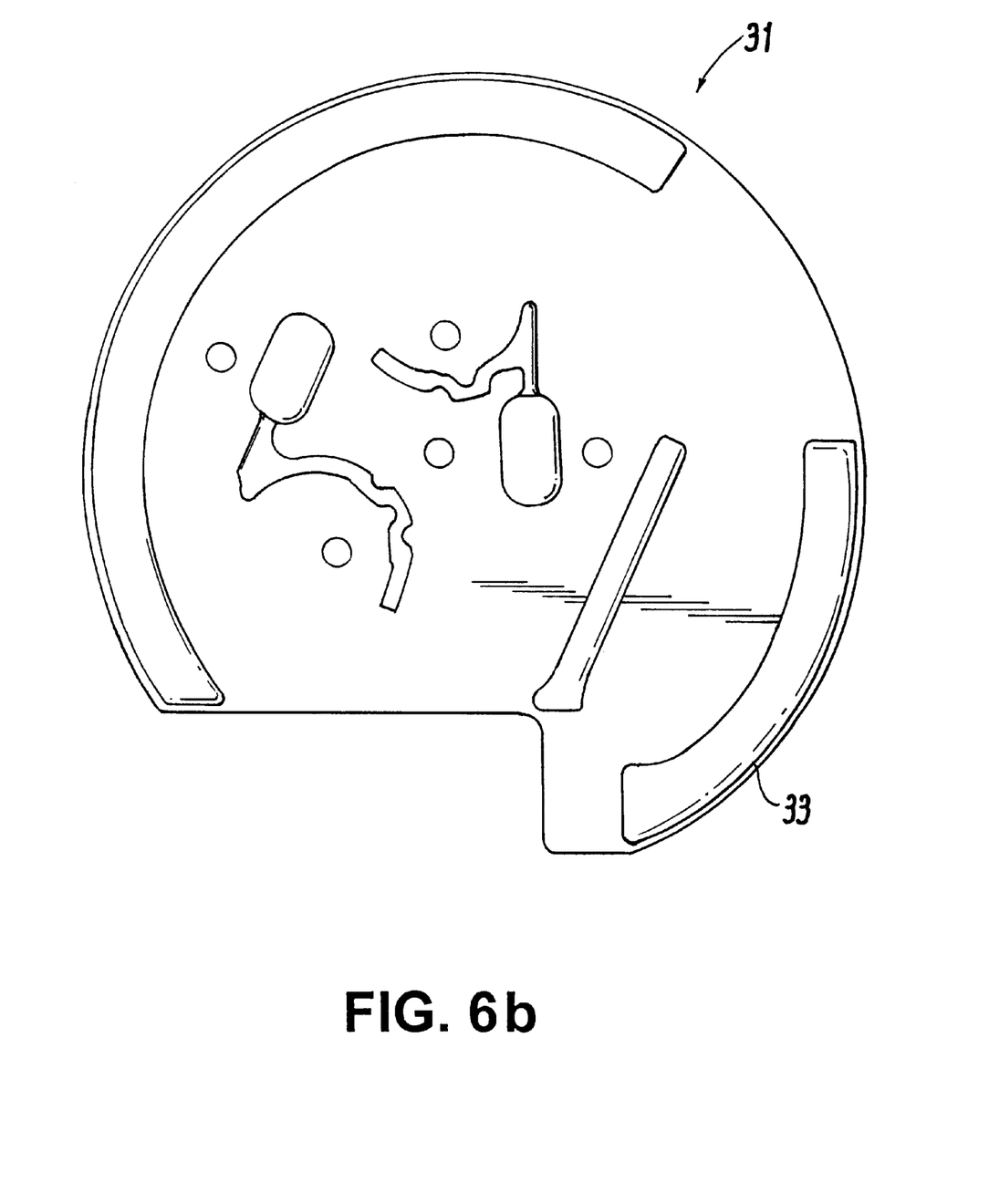

For the reasons explained in the foregoing, the use of a pre-curved papillotome is advantageous in maintaining the cutting surface in the desired cutting plane, i.e., the "12 o'clock" position. The sheath, however, is made of plastic and with time tends to loosen or relax its pre-curved configuration which, of course, deprives the papillotome of this advantage. It has been discovered that if the papillotome is shipped and stored in a package which retains the precise tip configuration desired until just before use, the preformed curvature is readily maintained for all normal usage of the papillotome. FIG. 6a and 6b show a unique package which functions to retain the desired curvature during transit and storage of the illustrated papillotome.

Referring to FIGS. 6a and 6b, a preferred curve retention package 31, in accordance with the invention, comprises first and second trays 32 and 33, for example formed from medical grade Kodar PETG 6763 C0007 (Eastman Chemical) Copolyester. The preferred outer dimensions of the packaging device 31 are approximately 11½"×11½"× 1¼" with a minimum tray thickness of 0.008". The first tray 32 comprises a handle opening 34, a circular channel 35 and first and second pre-curved tip channels 36 and 37. The handle opening 34 contains handle 12 while the sheaths 11 and 11a are contained by the circular channel 35. The first pre-curved tip channel 36 contains pre-curved tip 15 while the second channel 37 is utilized in the packaging of a shorter papillotome (which does not contain the lumen 16).

The important feature of the package 31 is the ability to retain the curvature of the tip 15. The pre-curved tip channels 36 and 37 are configured with the same continuous curve as found on the shape memory mandrel 30 (FIG. 5) used to form the pre-curved tip 15. Thus, the tip's shape memory curve is maintained during shipping and handling prior to actual use by the curve retention package 31. This has been found to be important, since if the pre-curved tip does not maintain its proper curvature for a prolonged period prior to use, the curve tends to relax which can vitiate the advantages of the invention.

Figures 7, 8, 9:
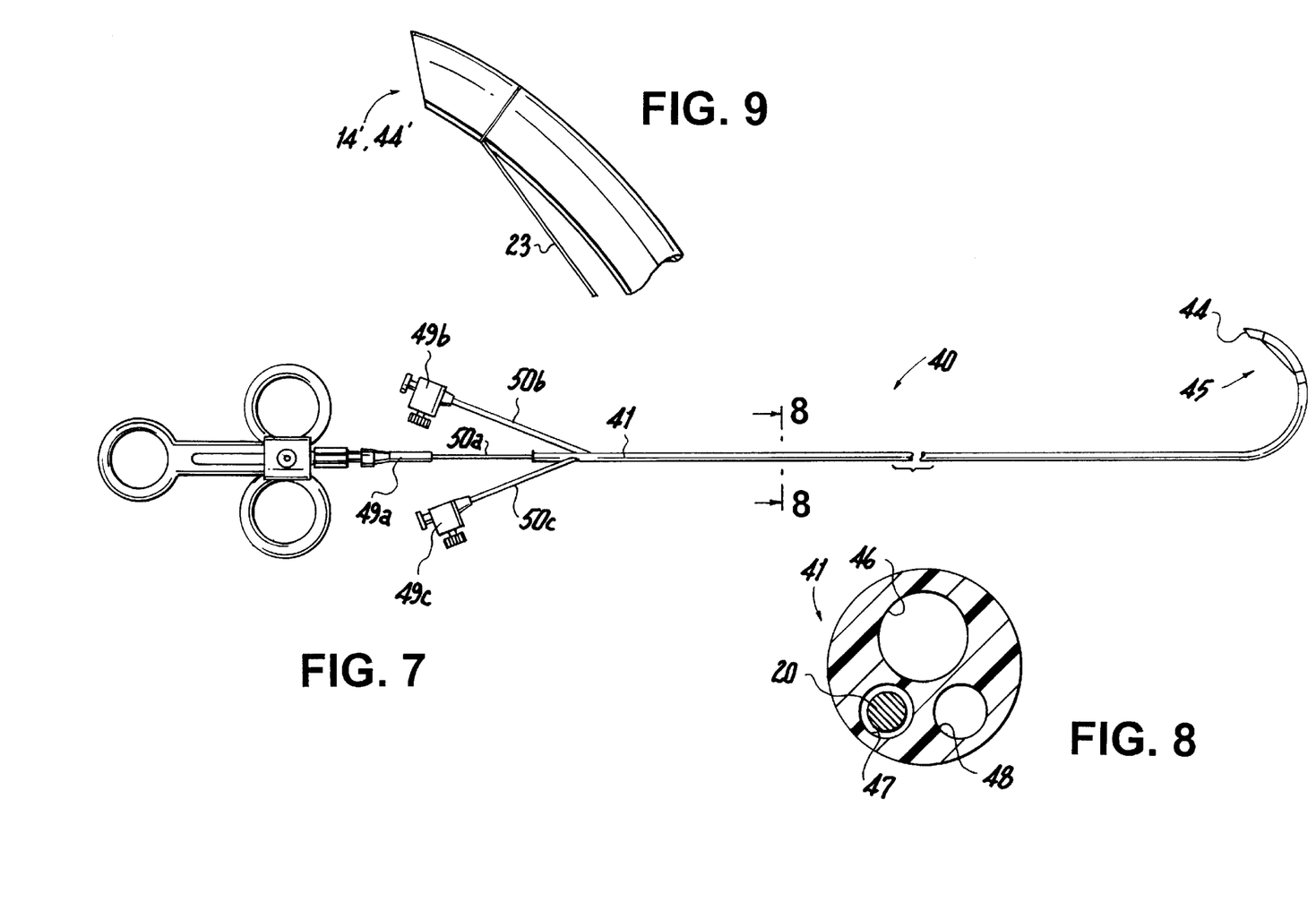
FIG. 7 is a perspective view of a papillotome according to a second embodiment of the invention.
FIG. 8 is a cross sectional view of the papillotome along line 8—8 of FIG. 7.
FIG. 9 is an enlarged side view of a modified distal tip which may be provided to a papillotome according to the invention.

Referring now to FIGS. 7 and 8, a sphincterotome or papillotome 40 is shown having a pre-curved shape memory tip 45 in accordance with a second embodiment of the present invention. The second embodiment differs from the first in that the papillitome 40 comprises a single sheath 41 having proximal and distal ends 43 and 44 and plural lumens. In all other respects, however, the second embodiment is structurally the same as the first embodiment, described in detail above. Moreover, the pre-curved tip 45 is preferably housed in a curve retention package 31, as described above, to better prevent the tip from relaxing to a different shape.

As can be seen in the cross-sectional view of FIG. 8, the papillitome of this embodiment has three side-by-side lumens 46, 47, 48 which extend parallelly between the proximal and distal ends 43 and 44. As in the first embodiment, the first and second lumens 46, 47 are for the guidewire and wire 20, respectively. The third lumen 48 may be dedicated for the delivery of a fluid, such as fluoroscopic contrast media, to supply the contrast media into the patient through the first lumen 48. The third lumen is generally disposed along the outside arc of the pre-curved tip 45 and terminates at an open end at or near the distal tip 44. The lumen is configured to deliver a fluid such as contrast to assist the operator in visualizing ahead of the billiary duct, for example).

At or near the proximal end 43 of the papillitome 40 are fittings 49a, 49b, and 49c (e.g., luer connectors). The fittings 49 are molded onto one end of respective segments of hypodermic tubing (hypotube) 50a, 50b, and 50c. The other end of the hypotubes is press fit into a respective one of the lumens 46, 47, 48. In the embodiment shown in FIG. 7, the manipulator control handle 12 is connected to fitting 49a and press fit into the lumen 47 at the proximal end 43 of the shaft 41, the fitting 49b for receiving the guidewire is press-fit into the lumen 46 a short distance from the proximal end 43 through a notch formed in the wall of the shaft 41 (e.g., using a knife blade), and the fitting 49c for receiving a syringe or other fluid delivery source is press-fit into the lumen 48 at a location somewhat further from the proximal end 43 than the fitting 49b also via a notch in the wall of the shaft 41. It is to be understood, however, that the particular location of the fittings 49a, 49b, and 49c is not pertinent to the invention. The lumen 46 for the guidewire is preferably larger than lumens 47 and 48.

FIG. 9 shows a modified distal tip 14' and 44' which may be provided to a papillotome 10 and 40, respectively, to ease cannulation of a sphincter (e.g., the papilla). In FIG. 9, the distal tip 14', 44' has been cut at an angle of about 30 degrees to about 60 degrees relative to the plane which contains the bend of the pre-curved tip 15, 45. This provides a smaller profile at the tip of the papillitome. An angle of about 45 degrees has been found to be suitable for easing cannulation.

As can be appreciated from the foregoing, the pre-curved tip end 15, 45 may consist solely of a flexible, non-metallic material provided that the material is settable when the tip end material when said tip end is relaxed. In this case, the tip end may consist solely of a flexible, non-metallic material.

While the embodiment of the invention shown and described is fully capable of achieving the results desired, it is to be understood that this embodiment has been shown and described for purposes of illustration only and not for purposes of limitation. Therefore, the invention is limited only by the appended claims.

What is claimed is:

1. A traction-type papillotome for use with an endoscope, comprising:

an elongated sheath having a distal tip end consisting solely of a flexible non-metallic material, a portion of said distal tip end having a first length and including a curve set in the material when said distal tip end is relaxed;

said sheath having a first lumen extending along at least a part of its length; and a wire of electrically conductive material in said first lumen having one end to be connected to a source of current and a cutting wire section at its other end that extends outwardly of the sheath between a first point on the inner radius of the curve and a second point on the inner radius of the curve of said distal tip end, the distance between said first and second points being less than said first length such that the cutting wire is exposed along only a portion of the curved distal tip end, said curved distal tip end including a curved portion proximal to said cutting wire section, the distal tip end being curved such that the cutting wire automatically orients to the 12 o'clock position when the traction-type papillotome emerges from the endoscope.

2. A papillotome as in claim 1, wherein said cutting wire section comprises a separate piece of wire electrically connected to said wire in said sheath first lumen.

3. A papillotome as in claim 1, further comprising means for applying a force to said wire to exert force on the tip end to change the shape of the curve of said tip end.

4. A papillotome as in claim 1, wherein said sheath includes a second lumen having an exit opening at a point along the length of the sheath.

5. A papillotome as in claim 4, wherein said sheath includes a third lumen which is isolated from said first and second lumens.

6. A papillotome as in claim 5, wherein said third lumen extends substantially the entire length of the sheath.

7. A papillotome as in claim 1 in combination with an elongated endoscope having a lumen, said sheath being movable within said endoscope lumen along its length with the curve of the tip end being straightened when within the endoscope lumen and said tip end upon exiting the endoscope resuming the curve shape.

8. The papillotome as in claim 1, wherein said cutting wire section includes a portion affixed to the curved distal tip end of the sheath.

9. A traction-type papillotome kit for use with an endoscope, comprising:

an elongated sheath having a distal tip end consisting solely of a flexible non-metallic material, a portion of said distal tip end having a first length and including a curve set in the material when said distal tip end is relaxed;

said sheath having a first lumen extending along at least a part of its length;

a wire of electrically conductive material in said first lumen having one end to be connected to a source of current and a cutting wire section at its other end that extends outwardly of the sheath between a first point on the inner radius and a second point on the inner radius of the curve of said distal tip end, the distance between said first and second points being less than said first length such that the cutting wire is exposed along only a portion of the curved distal tip end, said curved distal tip end including a curved portion proximal to said cutting wire section, the distal tip end being curved such that the cutting wire automatically orients to the 12 o'clock position when the traction-type papillotome emerges from the endoscope; and a package for said papillotome, said package including curve retention means for retaining said pre-curved shape memory tip in said set curve shape while said papillotome is in said package.

10. The papillotome kit as in claim 9, wherein said curve retention means comprises first and second trays and wherein said first tray has at least one channel formed in the configuration of the curve shape of the tip end.

11. The papillotome as in claim 9, wherein said cutting wire section includes a portion affixed to the curved distal tip end of the sheath.

12. A traction-type papillotome for use with an endoscope, comprising:

an elongated sheath having a distal tip end shaped to have a curve set in the material when said distal tip end is relaxed, a portion of said distal tip end having a first length;

said sheath having a first lumen extending along at least a part of its length;

said sheath having second and third lumens extending substantially to said distal tip end, at least one of said second and third lumens being sized to receive a guidewire; and a wire of electrically conductive material in said first lumen having one end to be connected to a source of current and a cutting wire section at its other end that extends outwardly of the sheath between a first point on the inner radius of the curve and a second point on the inner radius of the curve of said distal tip end, the distance between said first and second points being less than said first length such that the cutting wire is exposed along only a portion of the curved distal tip end, said curved distal tip end including a curved portion proximal to said cutting wire section, the distal tip end being curved such that the cutting wire automatically orients to the 12 o'clock position when the traction-type papillotome emerges from the endoscope.

13. The papillotome as in claim 12, wherein said cutting wire section includes a portion affixed to the curved distal tip end of the sheath.

14. A traction-type papillotome, comprising:
   an elongated catheter having a normally curved distal tip end when said distal tip end is relaxed;
   a first lumen extending within at least a first portion of the catheter; and
   a wire of electrically conductive material disposed in said first lumen and having a cutting wire segment extending exteriorly of the catheter between first and second locations on the catheter,
   said curved distal tip end including a proximal curved portion and a distal curved portion, said cutting wire segment extending exteriorly of the catheter only along said distal curved portion.

15. The papillotome as in claim 14, wherein said cutting wire segment includes a portion affixed to the curved distal tip end of the catheter.

16. The papillotome as in claim 14, further comprising a package for said papillotome, said package including curve retention means for retaining said normally curved distal tip end while said papillotome is in said package.

17. The papillotome as in claim 16, wherein said cutting wire segment includes a portion affixed to the curved distal tip end of the catheter.

* * * * *

UNITED STATES PATENT AND TRADEMARK OFFICE
CERTIFICATE OF CORRECTION

PATENT NO. : 6,017,340
DATED : January 25, 2000
INVENTOR(S) : Todd Cassidy

It is certified that error appears in the above-identified patent and that said Letters Patent is hereby corrected as shown below:

Title page, item [75], Assignees, change "MURRAY HILL N.J." to --RURAL HALL, N.C.--. and "RURAL HALL, N.C." to -- MURRAY HILL N.J.--.

Signed and Sealed this

Twenty-sixth Day of December, 2000

Attest:

Q. TODD DICKINSON

Attesting Officer

Director of Patents and Trademarks